US011537405B2

(12) United States Patent
Nguyen et al.

(10) Patent No.: US 11,537,405 B2
(45) Date of Patent: *Dec. 27, 2022

(54) SYSTEM AND METHOD FOR ACTIVATING A REPLACEMENT COMPONENT IN A MEDICAL DEVICE

(71) Applicant: Summit Imaging, Inc., Woodinville, WA (US)

(72) Inventors: Lawrence R. Nguyen, Woodinville, WA (US); James B. Taylor, Woodinville, WA (US)

(73) Assignee: Summit Imaging, Inc., Woodinville, WA (US)

( * ) Notice: Subject to any disclaimer, the term of this patent is extended or adjusted under 35 U.S.C. 154(b) by 5 days.

This patent is subject to a terminal disclaimer.

(21) Appl. No.: 16/777,481

(22) Filed: Jan. 30, 2020

(65) Prior Publication Data

US 2020/0167168 A1    May 28, 2020

Related U.S. Application Data

(62) Division of application No. 15/096,979, filed on Apr. 12, 2016, now Pat. No. 10,552,170.

(Continued)

(51) Int. Cl.
*G06F 9/44* (2018.01)
*G06F 9/4401* (2018.01)
(Continued)

(52) U.S. Cl.
CPC .......... *G06F 9/4403* (2013.01); *G06F 9/4411* (2013.01); *G06F 9/44505* (2013.01);
(Continued)

(58) Field of Classification Search
CPC ........ A61B 6/581; A61B 6/548; G16H 40/40; G16H 40/67; H05G 1/26; G06F 9/4403;
(Continued)

(56) References Cited

U.S. PATENT DOCUMENTS 7,107,189 B1 * 9/2006 Lounsberry .............. A61B 8/00
  702/188
8,650,055 B2    2/2014 Davie
(Continued)

OTHER PUBLICATIONS

Russakovskii, "How to: Manually Update Your Nexus 7 To Android 4.1.2 (JZ054K) With Stock Or Custom Recovery", Oct. 9, 2012, Android Police, 3 pages.

*Primary Examiner* — Danny Chan
(74) *Attorney, Agent, or Firm* — Seed IP Law Group LLP (57) ABSTRACT

A computer-implemented tool for use with an medical device having a computer system, the tool including an unsecured software-implemented suite of diagnostic tools and utilities configured to read logs, read system configuration provide a Telnet function, eject USB, and deactivate itself, and a secured software-implemented suite of diagnostic tools and utilities configured to interpret a key file received from an external source, upload the tool into the computer system of the medical device, run the tool upon booting up of the computer system to enable a replacement component in the medical device to be activated after installation in the medical device.

17 Claims, 6 Drawing Sheets

Related U.S. Application Data (60) Provisional application No. 62/149,309, filed on Apr. 17, 2015.

(51) Int. Cl.
*G16H 40/40* (2018.01)
*G06F 21/57* (2013.01)
*G06F 21/62* (2013.01)
*G06F 21/33* (2013.01)
*G06F 9/445* (2018.01)
*G06F 21/88* (2013.01)

(52) U.S. Cl.
CPC ............ *G06F 21/33* (2013.01); *G06F 21/575* (2013.01); *G06F 21/629* (2013.01); *G06F 21/88* (2013.01); *G16H 40/40* (2018.01)

(58) Field of Classification Search
CPC .... G06F 9/4411; G06F 21/575; G06F 21/629; G06F 21/33; G06F 9/44505; G06F 21/88
See application file for complete search history.

(56) References Cited

U.S. PATENT DOCUMENTS

| | | | |
|---|---|---|---|
| 9,064,117 B1 | 6/2015 | Worsley | |
| 2002/0095196 A1 | 7/2002 | Linberg | |
| 2002/0194531 A1 | 12/2002 | Lerman | |
| 2003/0014425 A1* | 1/2003 | Accardi | G16H 40/40 |
| 2003/0105389 A1 | 6/2003 | Noonan et al. | |
| 2004/0015956 A1* | 1/2004 | Barfield | G06F 8/62 |
| | | | 717/174 |
| 2004/0073276 A1 | 4/2004 | Samuelsson | |
| 2004/0120001 A1 | 6/2004 | Boldon | |
| 2004/0167465 A1 | 8/2004 | Mihai et al. | |
| 2005/0026486 A1* | 2/2005 | Thomas | H05K 7/1424 |
| | | | 439/188 |
| 2005/0071273 A1* | 3/2005 | Vroman | G06Q 30/06 |
| | | | 705/51 |
| 2006/0107119 A1 | 5/2006 | Miller et al. | |
| 2006/0111759 A1 | 5/2006 | Hoyme et al. | |
| 2006/0149126 A1* | 7/2006 | Ertas | A61B 1/00059 |
| | | | 600/101 |
| 2009/0252325 A1 | 10/2009 | Reus et al. | |
| 2010/0010646 A1 | 1/2010 | Drew et al. | |
| 2010/0161996 A1* | 6/2010 | Whiting | H04L 9/0877 |
| | | | 713/189 |
| 2011/0154006 A1* | 6/2011 | Natu | G06F 21/74 |
| | | | 713/2 |
| 2011/0179405 A1 | 7/2011 | Dicks et al. | |
| 2011/0185035 A1 | 7/2011 | Van | |
| 2011/0302461 A1* | 12/2011 | Goertler | G05B 23/0283 |
| | | | 714/57 |
| 2013/0053910 A1 | 2/2013 | Hareland | |
| 2013/0055230 A1 | 2/2013 | Kim | |
| 2013/0109323 A1 | 5/2013 | Ruutu et al. | |
| 2013/0125107 A1 | 5/2013 | Bandakka et al. | |
| 2013/0283030 A1 | 10/2013 | Drew | |
| 2013/0345623 A1* | 12/2013 | Kopperschmidt | A61M 1/3413 |
| | | | 235/494 |
| 2014/0380010 A1 | 12/2014 | Hogan et al. | |
| 2015/0094547 A1 | 4/2015 | Mickle et al. | |
| 2016/0260346 A1* | 9/2016 | Lafrinere | G09B 23/28 |
| 2018/0126171 A1 | 5/2018 | Herrmann et al. | |
| 2018/0214244 A1 | 8/2018 | Fuerstenberg et al. | |

\* cited by examiner

Unsecured: — 54

| |
|---|
| Read the System Configuration file. |
| Read log files. |
| Read the Product Code, System Serial # and System Options. |
| Read directly from the data port on a medical device. |
| Can safely eject a memory storage device plugged in via USB. |

Secured: — 56

| |
|---|
| Can allow the user to access the command prompt on the medical device. |
| Can activate a replacement component by resolving configuration issues and loading proper drivers on the medical device. |
| Can flash specific devices on a medical device. |
| Can back up or install the System Options file on a medical device. |

SYSTEM AND METHOD FOR ACTIVATING A REPLACEMENT COMPONENT IN A MEDICAL DEVICE

BACKGROUND

Technical Field

The present disclosure pertains to the service and repair of electronic equipment and, more particularly, to enabling operation of a repaired component by resolving errors and allowing activation following reinstallation of the repaired component in the electronic equipment.

Description of the Related Art

Modern electronic equipment employs numerous parts and components, such as circuit boards, that are interconnected and configured to carry out desired functions. Over time, components will require service and replacement. To ensure the electronic equipment functions properly, it is necessary to ensure that replacement components are the correct components and are authorized for installation and use on the equipment. Authorization can take several forms, including authorization through OEM personnel as well as automated authorization that takes place on the system itself, and a combination of authorization obtained from a technician or from the organization that owns the equipment of an independent service organization that is contracted by the organization that owns the equipment and via the automated system.

To this end, the electronic equipment is typically configured to recognize and permit operation of only authorized components. When a refurbished or replacement component is not recognized by the equipment's controller upon start-up, the controller will block the operation of the unrecognized component and, in most cases, generate an error code that is sent to an operator of the equipment.

In some situations a genuine replacement or refurbished component will not be automatically activated by the equipment. This can cause serious problems for the owner or user of the equipment, especially in the medical field. Equipment downtime can be costly to businesses and severely impair the ability of service entities to render services to those in need. Moreover, many customers have employees and technicians on staff to service the various devices used in diagnostics and evaluation of patients. For example, medical facilities such as hospitals service their own equipment and need the capability to quickly bring a machine back online. It is an FDA regulation that purchasers of such equipment be enabled to service their own equipment, but there are many road blocks through the OEMs to doing this. Hence, there is a need for a process that allows the operator to ensure the replacement component is activated by the equipment to resume normal operation.

BRIEF SUMMARY

The present disclosure is directed to the service and repair of medical device, such as medical imaging equipment. A system and method are provided to complete repair of the medical device by replacing the component. The system and method include a process configured to identify error codes in the medical device, clear the identified error codes, and activate a replacement component associated with the identified error codes in the medical device using external service tools. This includes reading errors and logs in the system to ensure it is returned to OEM specifications as required by law.

In accordance with one aspect of the present disclosure, a computer-implemented tool for use with a medical device having a computer system is provided. The tool includes an unsecured software-implemented suite of diagnostic tools and utilities configured to read error logs, read a build of materials, provide a Telnet function, eject USB, and to deactivate itself; and a secured software-implemented suite of diagnostic tools and utilities configured to interpret a key file received from an external source; upload and run upon booting up of the computer system of the medical device based on the key file, enable a replacement component in the medical device to be activated after installation in the medical device, and then delete or uninstall itself to restore a file structure back to OEM standards.

In accordance with another aspect of the present disclosure, the tool includes a communication circuit configured to communicate with the external source to receive the key file.

In accordance with yet another aspect of the present disclosure, a system is provided that includes a medical device having a controller with a control circuit and a memory in communication with the control circuit; a plurality of components in communication with the controller, the plurality of components including at least one replacement component; and a remote device capable of being in communication with the memory of the medical device and configured to communicate with the memory to enable the medical device to activate the at least one replacement component. The remote device includes a memory storage device having stored thereon a plurality of unsecured diagnostic and utility programs and a plurality of secured diagnostic and utility programs that are configured to be activated upon receipt of one or more key files; and software configured to receive the one or more key files to enable the use of secured functions of the secured diagnostic and utility programs to provide an enabling code to the medical device to be used to activate the at least one replacement component.

In accordance with still yet another aspect of the present disclosure, the system includes a remote provider configured to communicate with the remote device and provide the one or more key files to the remote device.

In accordance with a further aspect of the present disclosure, a method is provided for activating a component in a medical device, the method including the steps of: receiving a key file from an external source; uploading a protocol to a memory of the medical device; running the protocol as enabled by the key file, the protocol configured to enable the activation of one or more replacement components; and removing the protocol from the memory of the medical device after the one or more replacement components are activated.

In accordance with a further aspect of the present disclosure, the method further includes: reading an error log to identify and interpret error codes in the error log, identifying one or more replacement components in the medical device that are not activated, and clearing the error log based on the key file.

The advantages of the system and method of the present disclosure include very rapid response to malfunctions and error codes, lower downtime to mission critical equipment, and much lower cost to the user or owner of the equipment. Replacement components can be obtained for a fraction of the cost of OEM components, and this eliminates the need to outsource service calls.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures or components or both associated with the repair and replacement of components in medical device, medical imaging equipment, including but not limited to medical imaging equipment such as ultrasound machines, have not been shown or described in order to avoid unnecessarily obscuring descriptions of the implementations.

Unless the context requires otherwise, throughout the specification and claims that follow, the word "comprise" and variations thereof, such as "comprises" and "comprising" are to be construed in an open inclusive sense, that is, as "including, but not limited to." The foregoing applies equally to the words "including" and "having."

Reference throughout this description to "one implementation" or "an implementation" means that a particular feature, structure, or characteristic described in connection with the implementation is included in at least one implementation. Thus, the appearance of the phrases "in one implementation" or "in an implementation" in various places throughout the specification are not necessarily all referring to the same implementation. Furthermore, the particular features, structures, or characteristics may be combined in any suitable manner in one or more implementations.

Figure 1:
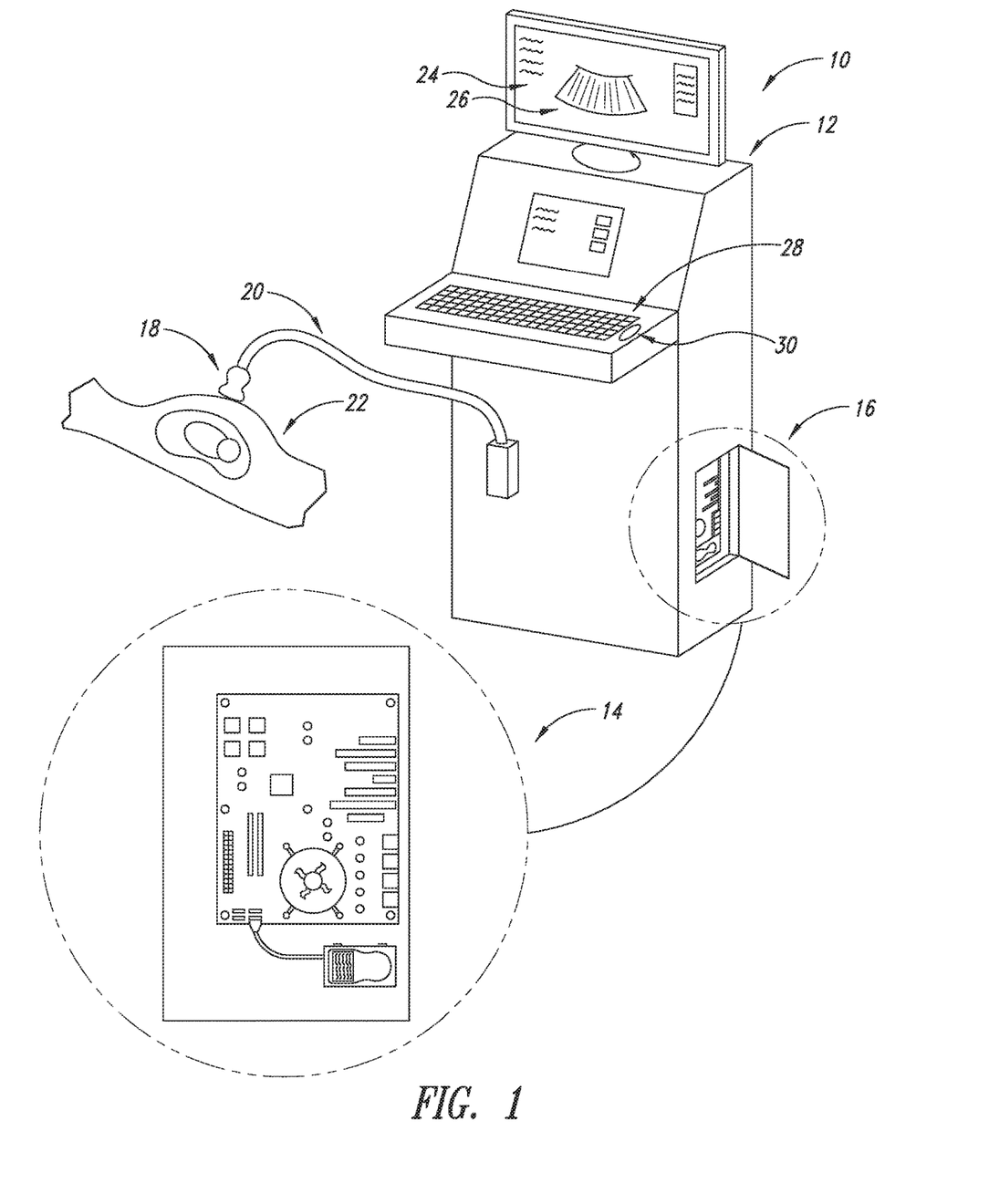
FIG. 1 illustrates a typical hardware environment in the form of a known medical device.

Referring initially to FIG. 1, shown therein is a representative illustration of a hardware environment in which the present disclosure is implemented. A medical device 10 is shown in the form of an ultrasound machine 12. It is to be understood that although the medical device 10 is described in the context of an ultrasound machine, it is intended to embrace all types of computerized equipment, including without limitation medical imaging equipment and related components, such as a transducer head for use with ultrasound machines.

As shown in FIG. 1, the ultrasound machine 12 typically includes a computer 14 or central processing unit (CPU) (shown schematically) that is mounted inside a housing 16 and configured to control operation of the ultrasound machine 12, perform calculations, and control the electrical power supplies for itself and the remote transducer probe 18. The probe transmits pulses or sound waves into the medium of interest, and it also receives the echoes that are converted to electrical pulses, which in turn are sent from the probe 18 to the computer 14, i.e., the CPU. The CPU performs the calculations involved in processing the data and forming an image for display.

The remote transducer probe 18 is coupled to the medical device 12 via a cable 20 and is configured to send the sound waves into a patient 22 and to receive the echoes of the sound waves. A transducer pulse control system is provided (not shown) that enables an operator to change the amplitude, frequency and duration of the sound waves or pulses emitted from the transducer probe 18. A display device 24, such as a monitor, displays the image 26 from the ultrasound data processed by the computer 14. Typically a user interface device, such as a keyboard 28 or mouse 30 or both, is included to input data and commands to the computer 14 and to facilitate taking measurements from the display device 24. Also included is a memory storage device (not shown), such as disk storage device (hard drive, floppy disk, CD), solid-state drive, or other types of memory devices that store the acquired images, and an output device (not shown) in the form of a display device or a printer that prints the image or selected aspects of the image from the display device. A remote server may also be utilized to store the acquired images.

Ultrasound has been adopted for a variety of clinical settings, including obstetrics and gynecology, cardiology and cancer detection. A chief advantage of ultrasound is that certain tissues can be observed without using radiation, such as in X-ray equipment. Ultrasound can also be done much faster than X-rays or other radiographic techniques.

However, ultrasound machines are subject to malfunctions and component failures as are other electronic equipment. High temperatures, age, component quality and other factors affect the operational reliability and life span of circuit boards and discrete components on the boards, transducer heads, cables, display devices and associated hardware. Over time, it may be necessary to replace one or more boards and components with new or refurbished components.

In accordance with the system and method of the present disclosure, a diagnostic and utilities tool, also referred to herein as the tool 50, is provided as shown and described more fully below in connection with FIGS. 2-6.

In accordance with implementation, the tool is a computer-implemented tool for use with a replacement component in a medical device having a computer system. The tool 50, as described more fully below, includes an unsecured software-implemented suite of diagnostic tools and utilities configured to communicate with the computer system of the medical device to read logs, read a bill of materials, provide a Telnet function, eject USB, and deactivate itself. In addition, the tool 50 includes a secured software-implemented suite of diagnostic tools and utilities configured to interpret a key file received from an external source, upload the tool into the computer system based on the key file, run the tool upon booting up of the computer system, and enable the replacement component in the medical device to be recognized and activated after installation in the medical device FIG. 2 is a block diagram of the system of the present disclosure in the context of a technician's computer 52 hard-wired to a memory storage device of a medical device.

The tool 50 is installed on a technician's computer 52. The tool 50 has two modules, an unsecured module 54 and a secured module 56, both of which are further illustrated in FIG. 4. Briefly, the unsecured module 54 contains an unsecured software-implemented suite of diagnostic tools and utilities configured to read logs, read a bill of materials, provide a Telnet function or other remote communications protocol to communicate with the medical device computer, eject USB for safely removing the memory storage device from the technician computer 52, and deactivate itself. The secured module 56 is a secured software-implemented suite of diagnostic tools and utilities configured to interpret a key file received from an external source 46, and enable a replacement component in the medical device to be activated, upload at least a portion of the tool into the medical device computer system (e.g., computer 14) based on the key file, run the tool upon booting up of the medical device computer system, and remove or uninstall itself after installation of the replacement component is complete. Uploading a portion of the tool to the medical device may be referred to as uploading a protocol to the medical device based on the key file.

Figure 2:
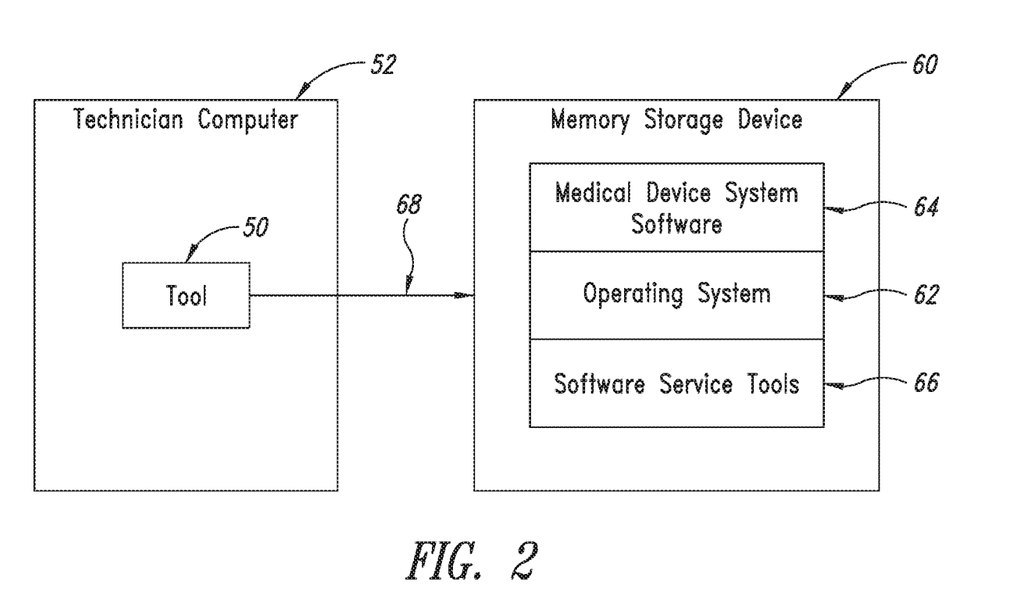
FIG. 2 is a block diagram of the system of the present disclosure in the context of a technician's computer hardwired to a memory storage device of an ultrasound machine.

Also shown in FIG. 2 is the memory storage device 60 of the computer 14 on which is installed an operating system 62, medical device system software 64 (e.g., ultrasound imaging software), and software service tools 66 (e.g., firmware), which are coupled to the operating system 62. An external connection 68 is provided, such as in the form of a cable, to enable communications between the technician's computer 52 and the operating system 62 on the memory storage device 60.

Figure 3:
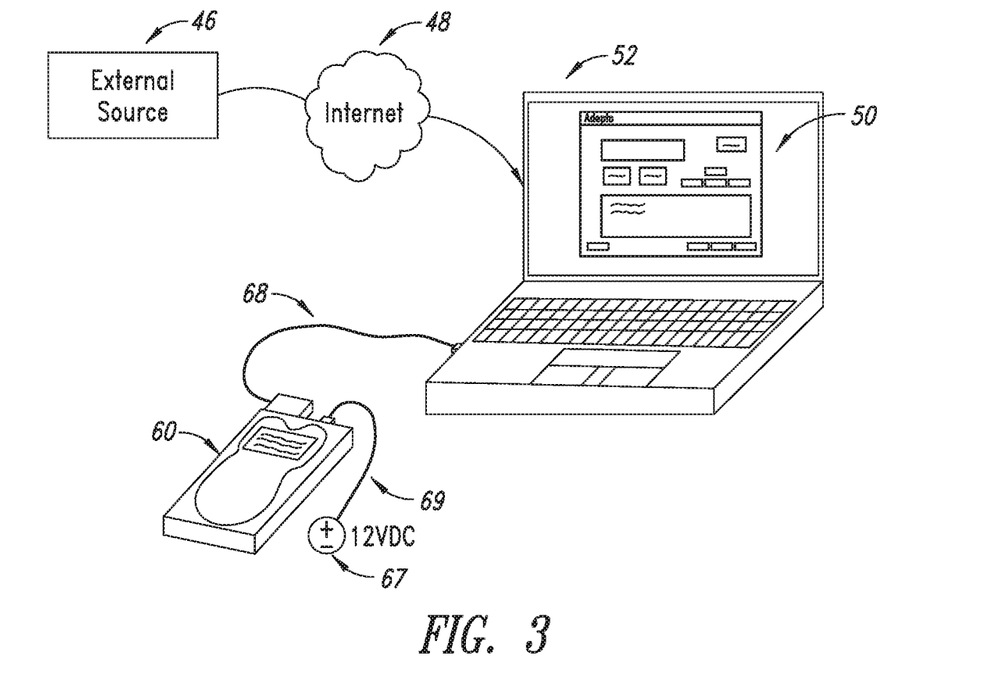
FIG. 3 is an external view of the hardware environment of FIG. 2.

FIG. 3 provides an external hardware view of these connections. Here, the memory storage device 60 is removed from the ultrasound machine 12 and powered by an external source 67 via a power cord 69. For example, the power cord 69 may be plugged into a standard 120V wall outlet and include circuitry to supply the proper voltage to the memory storage device 60. It is to be understood that the hard wired electrical connection between the memory storage device 60 and the technician computer 52 can instead be accomplished via a wireless communication scheme, such as Bluetooth® or Wi-Fi or other known radio frequency communication method. Alternatively, the technician computer 52 can be electrically connected to the memory storage device 60 while it is still in the ultrasound machine 12 via a cable or wireless connection.

The tool 50 receives the key file from external source 46 via the internet 48 or some other network connection. The key file is then utilized by the tool 50 to determine which functions of the secure module 56 to employ. In some scenarios, a license from the external source 46 may be needed before the key file is obtained by the tool 50.

Figure 4:
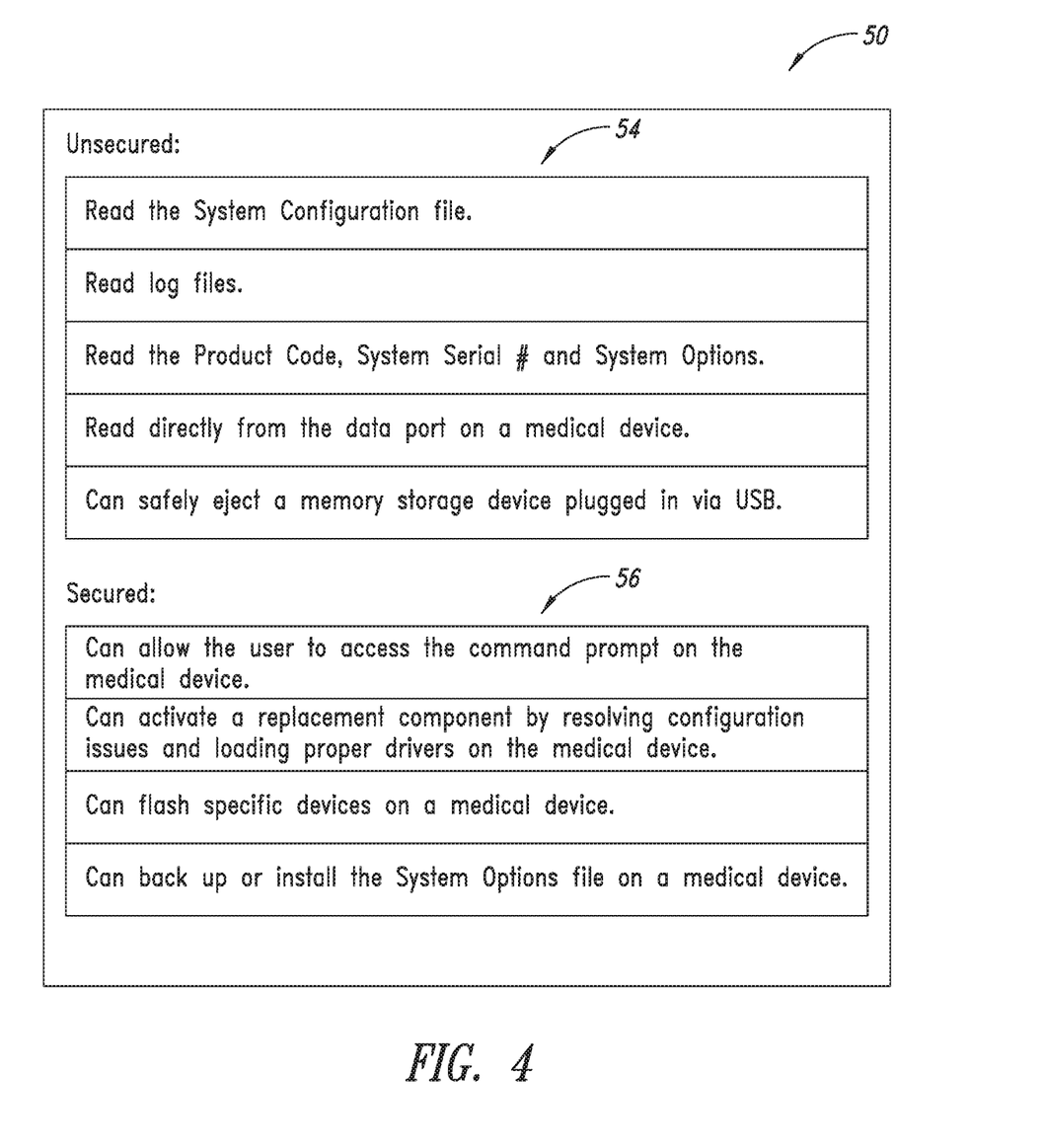
FIG. 4 illustrates in more detail the two modules of the tool formed in accordance with the present disclosure.

FIG. 4 illustrates in more detail the two modules of the tool 50 formed in accordance with the present disclosure. The unsecured module 54 includes, without limitation, diagnostic software that performs a variety of functions, including reading a system configuration file; reading an error log from the machine's memory storage device; reading the key file, system serial number, and system options; reading information from the front end of an ultrasound machine 12 using a serial port; and safely ejecting a memory storage device plugged in via a USB connection. The secured module 56 has functions that include allowing the user to access the system's command prompt; updating the system configuration and allowing components to be replaced; flashing specific devices on the machine 12; and backing up or installing the systems options for the machine 12.

Figure 5A:
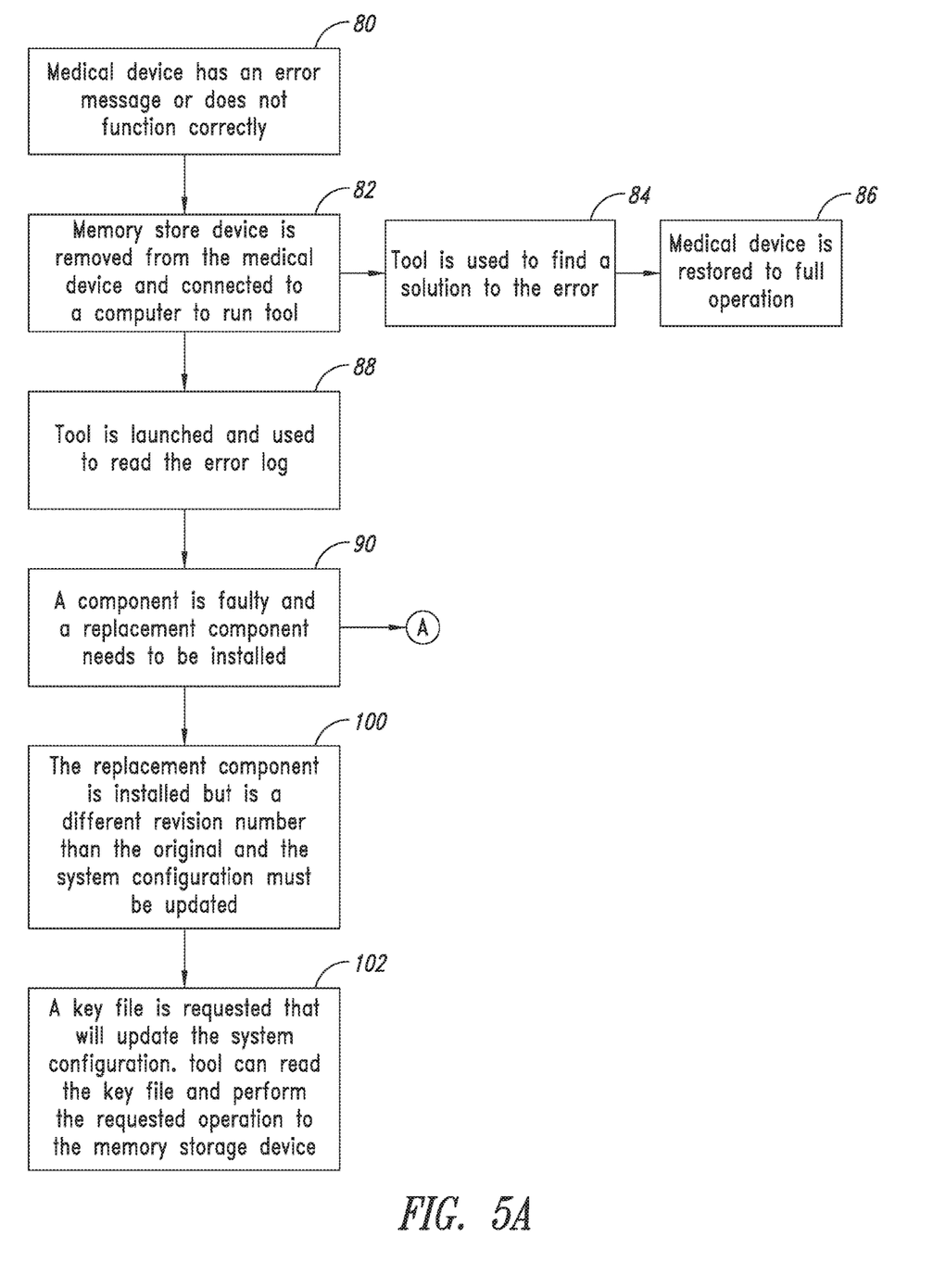
FIGS. 5A and 5B are a high-level overview of the process employed by the tool of the present disclosure.
Figure 5B:
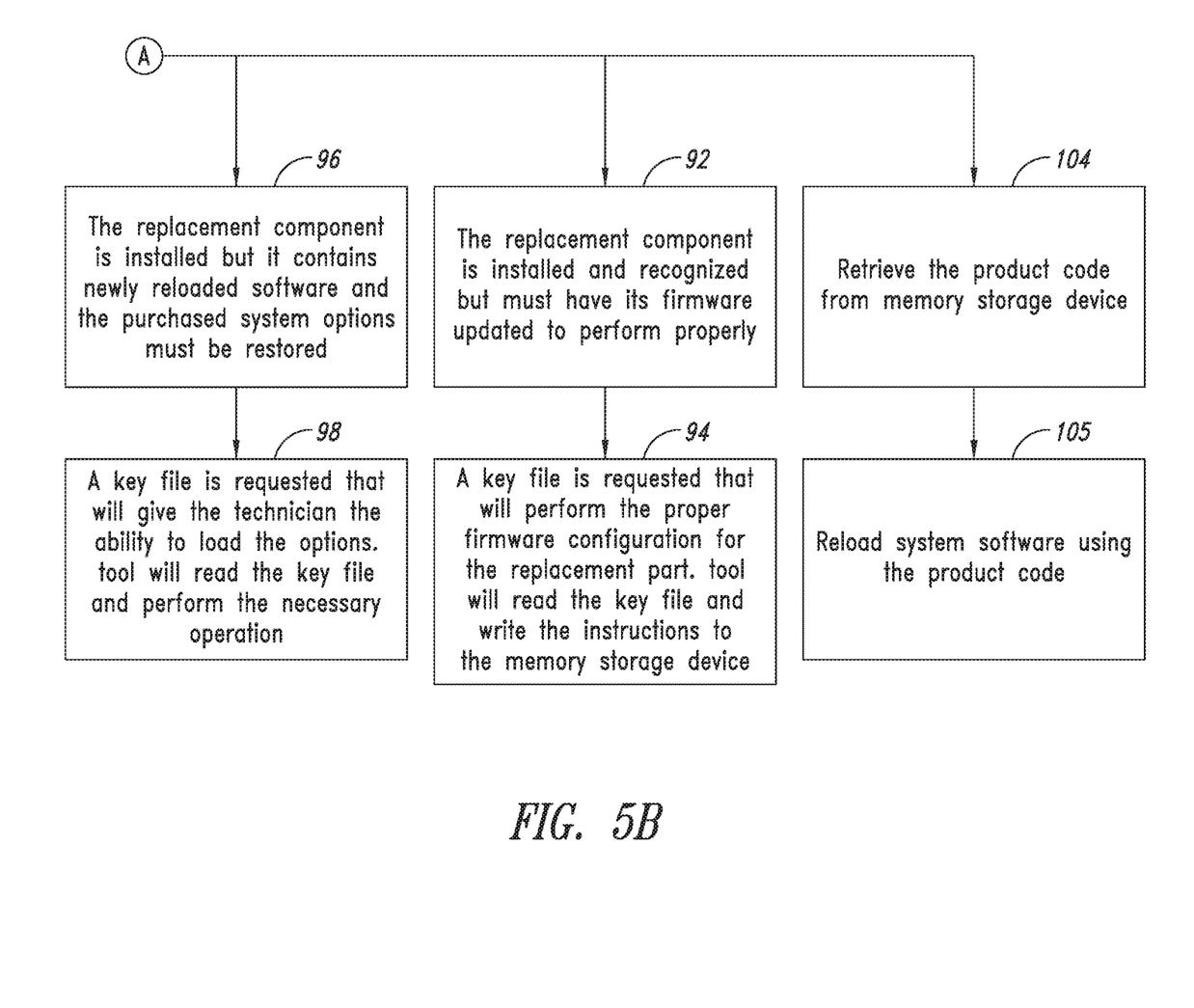

Referring next to FIGS. 5A and 56, shown therein is a high-level overview of the process employed by the tool of the present disclosure. Initially, at step 80, the medical device has an error message or does not function correctly. The on-site personnel remove the memory storage device from the machine and connects it to the computer in step 82. Once connected, the tool either immediately corrects the error or aids the personnel or a remote technician in correcting the error, as shown in step 84. The machine is then restored to full operation in step 86.

Alternatively, after the memory storage device is coupled to the computer in step 82, the tool is launched and used to read the Error Log (step 88) of the machine. If it is determined that a component is faulty and a replacement component needs to be installed in step 90, one of four things can happen.

First, the replacement component is installed and recognized but must have its firmware updated to perform properly (step 92), after which a key file is requested that will allow the tool to perform the proper firmware configuration for the requested replacement component. The tool will write the corrective instructions to the memory storage device in step 94 to update the firmware and enable the replacement component to properly function.

Second, the replacement component is installed but it contains newly reloaded software and the purchased system options must be restored (step 96). This is done in step 98 by requesting a key file, which will give the technician the ability to load the options on the replacement component. The tool will read the key file and perform the necessary operation load operation.

In a third scenario, the replacement component is installed but is a different revision number than the original component and the system configuration must be updated (step 100). Again, a key file is requested that will update the system configuration in step 102. The tool reads the key file and performs the requested operation to the memory storage device to enable the replacement component to perform its function within the system.

In a fourth scenario, the replacement component is installed but the system software needs to be reloaded. The produced code is retrieved from the memory storage device at step 104, and the system software is reloaded on to the replacement component using the retrieved product code at step 105. The replacement component is then able to function in accordance with design specifications within the context of the medical device in which it is installed.

After the tool performs the appropriate functions on the memory storage device, the memory storage device is reconnected to the medical device. The computer on the medical device is rebooted, and the tool functionality uploaded on the memory storage device can execute, which includes removing the tool from the memory device.

Figure 6:
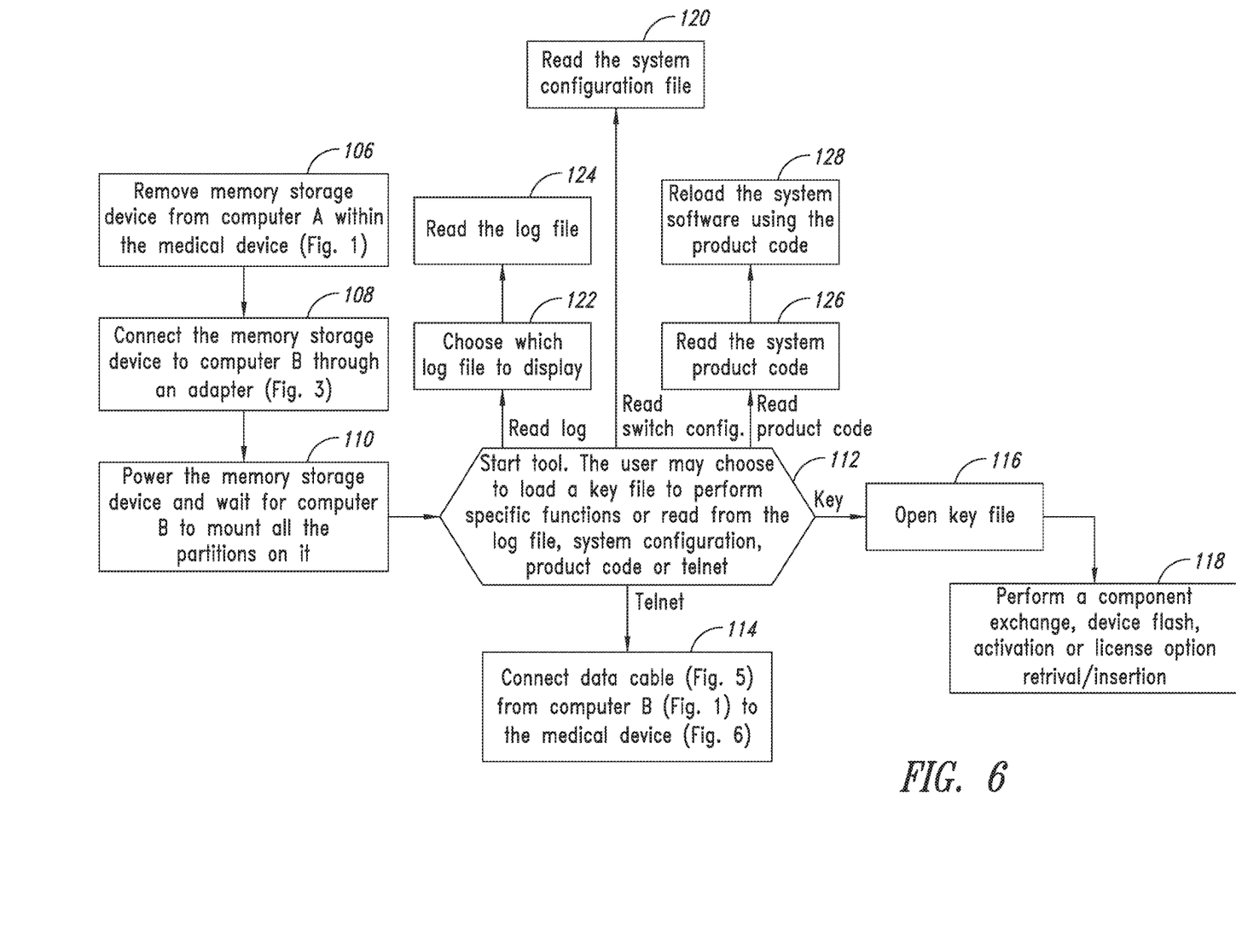
FIG. 6 illustrates a method for implementing the process of identifying and resolving error codes by activating a replacement component in the medical device.

FIG. 6 illustrates a process diagram of the method for implementing the process of identifying and resolving error codes and activating a replacement component in the medical device. In an initial step 106, the memory storage device is removed from the medical device and connected to a USB adapter and power is supplied by a power adaptor. The USB connector is connected to the technician's computer in step 108, and power is applied to the memory storage device. The tool on the technician's computer then accesses and recognizes the memory storage device.

The technician then starts the tool in step 112. It is at this point the technician may choose to load a key file to perform specific functions or read from the Log or System Configuration or Telnet. The functionality available to the technician is, for example, shown in FIG. 4. For example in step 114, if Telnet is used, the cable is coupled to the serial port or other suitable port on the medical device and the unsecured module only is available to the technician.

Alternatively, in step 116, the key file is opened, and then the tool is used to perform a device flash or product activation as shown in step 118. This is the secured module of the tool as described above with the functionality shown in the table in FIG. 4. These steps can only be done if the memory storage device is connected to the technician's computer.

If the memory storage device is removed from the medical device, then the process shown in steps 120, 122, and 124 would be implemented. More particularly, using the unsecured functionality of the tool, the system configuration file can be read in step 120. Or, the Error Log can be read wherein the technician can choose which Error Log to display in step 122 and to read it in step 124. Or, the product code can be read in step 126 from the memory storage device, and the system software is reloaded at step 128 using the product code.

The various implementations described above can be combined to provide further implementations. Aspects of the implementations can be modified, if necessary to employ concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A system, comprising:
   a medical device that includes:
      a controller having a control circuit and a memory in communication with the control circuit; and
      a plurality of components in communication with the controller, the plurality of components including a hardware component to be replaced by at least one replacement component; and
   a remote device capable of being in communication with the memory of the medical device and configured to communicate with the memory to enable the medical device to activate the at least one replacement component, the remote device including:
      a memory having stored thereon:
         a plurality of unsecured diagnostic and utility programs and a plurality of secured diagnostic and utility programs that are configured to be activated upon receipt of one or more key files; and
         a software program that, when executed by the remote device, is configured to receive the one or more key files to enable the use of secured functions of the secured diagnostic and utility programs to provide an enabling code to the memory of the medical device to be used to activate the at least one replacement component,
      wherein:
         prior to replacing the hardware component, a program of the plurality of unsecured diagnostic and utility programs evaluates a log of the medical device to identify that the hardware component is associated with a fault, and
         the secured functions of the secured diagnostic and utility programs enable clearing the log.

2. The system of claim 1, further comprising a remote provider configured to communicate with the remote device and provide the one or more key files to the remote device.

3. The system of claim 1, wherein a secured diagnostic and utility program of the plurality of secured diagnostic and utility programs, when executed by the remote device, causes the remote device to:
   upload a portion of the secured diagnostic and utility program into the memory of the medical device.

4. The system of claim 3, wherein the uploaded portion of the secured diagnostic and utility program is run upon booting up of the controller in the medical device.

5. The system of claim 3, wherein the uploaded portion of the secured diagnostic and utility program enables the at least one replacement component to be recognized and activated after physical installation of the at least one replacement component in the medical device.

6. The system of claim 5, wherein enabling the at least one replacement component to be recognized and activated includes updating a system configuration of the at least one replacement component.

7. The system of claim 1, wherein a secured diagnostic and utility program of the plurality of secured diagnostic and utility programs, when executed by the remote device, causes the remote device to:
   load in the medical device a system software for performing operations.

8. The system of claim 7, wherein after the system software is loaded, a portion of a secured diagnostic and utility program of the plurality of secured diagnostic and utility programs upload into the memory of the medical device removes or uninstalls itself and restores the controller to original equipment manufacturer standards.

9. The system of claim 1, wherein the one or more key files are representative of functions of a secured diagnostic and utility program of the plurality of secured diagnostic and utility programs.

10. The system of claim 9, wherein the remote device utilizes the one or more key files to determine which functions of the secured diagnostic and utility program of the plurality of secured diagnostic and utility programs to employ.

11. The system of claim 1, wherein the at least one replacement component has a different revision number than a replaced hardware component.

12. The system of claim 1, wherein an unsecured diagnostic and utility program of the plurality of unsecured diagnostic and utility programs, when executed by the remote device, causes the remote device to:
   read a bill of materials;
   provide a teletype network function;
   eject USB; and
   deactivate itself.

13. The system of claim 1, wherein the plurality of components include a communication circuit configured to communicate with a remote provider to receive the one or more key files.

14. The system of claim 13, wherein receiving the one or more key files is contingent upon a license.

15. A method of a recognizing and activating one or more hardware replacement components in a medical device, the method comprising:
   prior to replacing a hardware component, evaluating a log of the medical device to identify that the hardware component is associated with a fault;

replacing the hardware component;
receiving a key file from an external source;
uploading a software program to a memory of the medical device;
running the software program as enabled by the key file to enable activation of a hardware replacement component;
clearing the log; and
removing the software program from the memory of the medical device after the hardware replacement component is activated.

16. The method of claim 15, further comprising:
activating a plurality of unsecured diagnostic and utility programs and a plurality of secured diagnostic and utility programs in a remote device based on the key file.

17. The method of claim 15, further comprising:
providing an enabling code to enable the activation of one or more replacement components.

* * * * *